United States Patent [19]

Van Dijck et al.

[11] Patent Number: 4,648,988

[45] Date of Patent: Mar. 10, 1987

[54] WATER-DILUTABLE WOOD-PRESERVING LIQUIDS

[75] Inventors: Paul C. M. Van Dijck, Brecht; Theo F. M. C. Ligtvoet, Vlimmeren; Leo J. J. Van Leemput, Wakkerzeel-Haacht, all of Belgium

[73] Assignee: Janssen Pharmaceutica, N.V., Beerse, Belgium

[21] Appl. No.: 660,817

[22] Filed: Oct. 15, 1984

Related U.S. Application Data

[63] Continuation-in-part of Ser. No. 564,121, Dec. 21, 1983, abandoned.

[51] Int. Cl.$^4$ .................... C09D 5/18; C09K 21/00; C09K 21/10; C09K 21/08
[52] U.S. Cl. .................................. 252/602; 34/9.5; 106/18.21; 106/18.32; 252/607; 252/603; 548/262
[58] Field of Search ............... 106/18.33, 18.34, 18.32, 106/15.05, 18.11, 18.21, 18.22; 252/601, 602, 607, 603, 608, 398, 399, 400 R, 400 A, 401, 402, 403, 404, 405, 406; 34/9.5, 13.4, 13.8; 162/159–161; 548/262–263; 549/369, 430, 455; 424/1.1

[56] References Cited

U.S. PATENT DOCUMENTS

| | | | |
|---|---|---|---|
| 4,079,062 | 3/1978 | Van Reet et al. | 424/269 |
| 4,216,217 | 8/1980 | Van der Aa et al. | 424/263 |
| 4,380,546 | 4/1983 | Sauter et al. | 424/269 |
| 4,395,415 | 7/1983 | Hagen et al. | 424/263 |
| 4,411,687 | 10/1983 | Zeeh et al. | 71/94 |
| 4,464,381 | 8/1984 | Janssen et al. | 424/269 |

Primary Examiner—Stephen J. Lechert, Jr.
Assistant Examiner—Howard J. Locker
Attorney, Agent, or Firm—Geoffrey G. Dellenbaugh

[57] ABSTRACT

Wood-preserving liquids which are dilutable with aqueous mediums, said liquids containing a suitable solvent, a suitable solubilizer and an azole.

8 Claims, No Drawings

WATER-DILUTABLE WOOD-PRESERVING LIQUIDS

CROSS-REFERENCE TO RELATED APPLICATION

This is a continuation-in-part of our co-pending application Ser. No. 564,121, filed Dec. 21, 1983 now abandoned.

DESCRIPTION OF THE INVENTION

Since it is desirable to preserve wood from decay caused by microorganisms several compounds having antimicrobial properties have been described as useful wood-preserving agents.

As wood is considered, for example, wood products such as timber, lumber, railway sleepers, telephone poles, fences, wood coverings, wicker-work, plywood, particle board, waferboards, clipboard, joinery, bridges or wood products which are generally used in housebuilding.

Wood which is preserved from staining and decay is meant to be protected from moulding, rotting, loss of their useful mechanical properties such as breaking strength, resistance to shock and shearing strength, or decrease of their optical or other useful properties such as the occurrence of odor, staining, spot formation and dote caused by the following microorganisms: Aspergillus species, Penicillium species, *Aureobasidium pullulans, Sclerophoma pityophilla,* Verticillium species, Alternaria species, Rhizopus species, Mucor species, Paecilomyces species, Saccharomyces species, *Trichoderma viride, Chaetomium globosum, Stachybotrys atra, Myrothecium verrucaria, Oospora lactis* and other staining and wood decay fungi. Special emphasis should be led on the good activity against moulds and staining fungi such as *Aspergillus niger, Penicillium funiculosum, Trichoderma viride, Alternaria alternata,* decay and softrot fungi such as *Chaetomium globosum, Trychophyton mentagrophytes, Coriolus versicolor, Coniophora cerebella, Poria monticola, Merulius (Serpula) lacrymans* and *Lenzites trabea,* and yeasts such as *Candida albicans* and Saccharomyces species.

In order to protect wood from decay it is treated with formulations containing one or more wood-preserving agents. Such treatment is applied by several different procedures such as, for example, by treating the wood in closed pressure- or vacuum systems, in thermal- or dip systems and the like, or by a wide variety of exterior wood-structure treatments, e.g. by brushing, dipping, spraying or soaking the wood with the formulation containing the wood-preserving agent.

Whereas anorganic compounds were used as wood-preserving agents the more recently preferred agents are organic compounds, such as, for example, the azoles described in European Pat. No. 38,109. Due to their organic nature these compounds have rather lipophilic properties, resulting in a good solubility in organic mediums and an often inadequate solubility in aqueous mediums. Consequently these organic agents are usually incorporated in organic formulations for applying them to the wood.

However, these organic formulations have some less advantageous properties such as, for example, their expense combined with disadvantageous influences on the environment and the safety and health of the applicator. Therefore a number of organic liquids which form emulsions or dispersions with aqueous mediums have recently been developed, such as the organic liquids described in U.S. Pat. No. 4,357,163. However these emulsions or dispersions, formed after mixing the organic liquid with the aqueous medium, are known to be too liable to a number of factors, such as, for example, changes of temperature, pH of the mixture and/or hardness of the water used, the presence of impurities in the wood and the like, resulting in an often inadequate physical stability.

Additionally, because a rather invariable concentration of the active agent in the formulation is required to assure a continuous process in closed pressure- or vacuum systems or in thermal- or dip techniques, lack of uniform uptake of the suspension or dispersion by the wood negatively influences the applicability of said suspensions or dispersions in such techniques. Such lack of uniform uptake causes a decreasing or increasing concentration of the active agent in the remaining formulation, which may finally result in a dilution of the formulation respectively a precipitation of the wood-preserving agent.

The present invention is concerned with organic wood-preserving liquids which are dilutable with predominantly aqueous mediums, said liquids containing:

(i) from 10% to 80% of a suitable solvent;
(ii) from 20% to 80% of a suitable solubilizer; and
(iii) from 0.01% to 10% of at least one azole having the formula

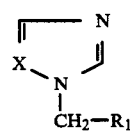   (I)

or an acid addition salt thereof, wherein X is nitrogen or a CH group and $R_1$ is a radical of the formula

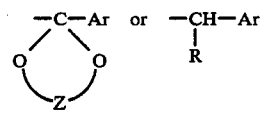

wherein Z is a group —$CH_2$—$CH_2$—, —$CH_2$—$CH_2$—$CH_2$—, —$CH(CH_3)$—$CH(CH_3)$— or —$CH_2$—$CH$(alkyl)—, wherein said alkyl is a straight or branched $C_1$-$C_{10}$ alkyl radical; said Ar is a phenyl group which is optionally substituted with 1 to 3 halogens, $C_1$-$C_6$ alkyl radicals, $C_1$-$C_6$ alkoxy radicals, cyano-, trifluoromethyl- or nitro groups, a thienyl-, halothienyl-, naphthalenyl- or fluorenyl group; and, said R is $C_1$-$C_{10}$ alkyl, cycloalkyl, cycloalkyllower alkyl, lower alkenyl, aryllower alkyl, aryloxylower alkyl or a radical of the formula —O—$R_o$, wherein said $R_o$ is $C_1$-$C_{10}$ alkyl, lower alkenyl, lower alkynyl or aryl-lower alkyl, wherein said aryl radical is phenyl, naphthalenyl or substituted phenyl, wherein said substituted phenyl has 1 to 3 substituents selected from the group consisting of halo, cyano, nitro, phenyl, lower alkyl and lower alkoxy, provided that when more than one substituent is present only one thereof may be cyano, nitro or phenyl.

The said wood-preserving liquids have the advantage that almost instantaneously homogeneous solutions are formed by mixing these liquids with predominantly aqueous mediums. Furthermore, these solutions have an extremely high physical stability, not only at ambient temperature, i.e. at temperatures comprised between 15° C. and 35° C., but also at decreased temperatures. Even after several cycles of crystallization of the aqueous solution below 0° C. and subsequent storage at ambient temperature the physical stability is not negatively influenced.

The homogeneous solutions combine also a good moistening of the wood-surface with a high degree of penetration of the said solutions in the wood, resulting in an unexpectedly high uptake of the solution by the wood, and, consequently, a desired preservation of the treated wood.

Additionally, due to a uniform uptake of the aqueous solution the wood-preserving liquids and the resulting aqueous solutions are particularly useful in treatment techniques which require the possibility of a continuous process, such as, for example, impregnation- or dip techniques.

Besides the previously cited advantages the subject compositions have also the advantage that the same protection of the treated wood is obtained at lower amounts of active ingredient taken up by the wood when aqueous solutions are used than when solvent-based mixtures are used.

In addition the solutions formed with the wood-preserving liquids combine the hereinabove mentioned advantages with those which are characteristic to predominantly aqueous mediums, such as, for example, a relatively high flashpoint, reduced toxicity resulting in advantageous influences on the environment and the health and safety of the applicator, lack of irritation and the like.

Particularly interesting liquids in accordance with the present invention are those containing an agent of formula

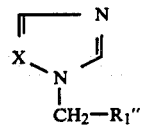
(I-a)

wherein X has the above-identified meaning and $R_1'$ is a radical of the formula

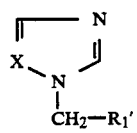

wherein Z' is a group $-CH_2-CH_2-$, $-CH_2-CH_2-CH_2-$, $-CH(CH_3)-CH_2-$, $-CH(C_2H_5)-CH_2-$, $-CH(C_3H_7)-CH_2-$, $-CH(CH_3)-CH(CH_3)-$ or $-CH(CH_3)-CH(C_2H_5)-$; Ar' is unsubstituted phenyl or phenyl substituted with 1 to 3 halogen atoms, preferably chloro atoms, $C_1-C_6$ alkyl radicals, $C_1-C_6$ alkoxy radicals, cyano or nitro groups; and R' is $C_1-C_6$ alkyl or $C_3-C_4$ alkenyloxy.

More particularly interesting liquids in accordance with the present invention are those containing an agent of formula

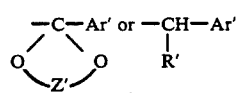
(I-b)

wherein X has the above-identified meaning and $R_1''$ is a radical of the formula

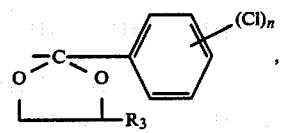

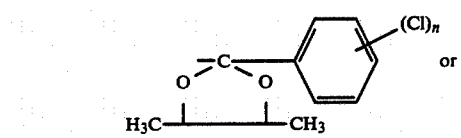 or

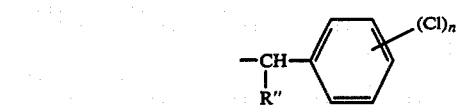

wherein R'' is $C_1-C_4$ alkyl, $C_3-C_4$ lower alkenyloxy, $R_3$ is hydrogen or $C_1-C_3$ alkyl and n is 1 or 2.

Preferred liquids in accordance with the present invention are those containing 1-[2-(2,4-dichlorophenyl)-1,3-dioxolan-2-ylmethyl]-1H-1,2,4-triazole, generically designated as azaconazole, or a suitable acid addition salt thereof.

As it is required that the wood-preserving liquid forms a homogeneous solution with a predominantly aqueous medium the solubilizer must sufficiently solubilize the active agent and the solvent of the liquid in the aqueous medium and may not negatively influence the solubility of the active agent in the solvent.

Preferred solubilizers are selected from the group consisting of:

(i) addition products of 1 to 60 moles of ethylene oxide with 1 mole of a phenol which is further substituted with at least one $C_1-C_{15}$ alkyl group; and (ii) addition products of 1 to 60 moles of ethylene oxide with 1 mole of ricinus oil.

The most preferred solubilizers are selected from the group consisting of:

(i) addition products of 1 to 60 moles of ethylene oxide with 1 mole of nonylphenol or octylphenol; and (ii) addition products of 1 to 60 moles of ethylene oxide with 1 mole of ricinus oil.

The organic solvent of the liquid must fulfill the requirements of sufficiently solubilizing the active ingredient and, combined with the solubilizer, being homogeneously miscible with a predominantly aqueous medium.

Preferred solvents are 2-butoxyethanol and butyl 2-hydroxyacetic acid ester.

In the formulations of the present invention the azoles of formula (I) can also be used in combination with other compounds having a useful activity such as, biocidal compounds, e.g. antimicrobial agents, insecticides and the like.

As antimicrobial agents, which may be used in combination with the azoles of formula (I) there may be considered products of the following classes:

Phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, chlorinated hydrodiphenylethers such as, for example, 2-hydroxy-3,2′4′-trichlorodiphenylether, phenylphenol, 4-chloro-2-phenylphenol, 4-chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; mono-, di- and polyamines such as dodecylamine or 1,10-di(n-heptyl)-1,10-diaminodecane; quaternary ammonium compounds such as benzyl-dimethyldodecylammonium chloride, dimethyldodecylammonium chloride, benzyl-di(2-hydroxyethyl)dodecylammonium chloride; sulfonium- and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercaptoquinoxaline-di-N-oxide, as well as the symmetrical disulfides of said mercapto compounds; ureas such as tribromo- or trichlorocarbanilide, dichloro-trifluoromethyldiphenylurea; tribromosalicylanilide; 2-bromo-2-nitro-1,3-dihydroxypropane; dichlorobenzoxazolon; chlorohexidine; isothia- and benzisothiazolone derivatives.

As insecticidal agents which may be used in combination with the azoles of formula (I) the following classes of products may be considered: insecticides having a natural origin, e.g., nicotine, rotenone, pyrethrum and the like; chloridinated hydrocarbons, e.g., lindane, chlordane, endosulfan and the like; organic phosphor compounds, e.g., diazinon, parathion, dichloorvos, dimethoate and the like; carbamates, e.g., carbaryl, aldicarb, methiocarb, propoxur and the like; biological insecticides, e.g., products originating from Bacillus thuringiensis; synthetic pyrethroids, e.g., permethrin, allethrin, cypermethrin, halothrin and the like.

Furthermore, the formulations of the subject invention may also contain additives which may improve their applicability, the chemical and/or physical stability and the like properties of the said formulations. Examples of such additives are naturally occuring and synthetic resins, e.g. wood resin, alkyd resin, polyurethane resin and the like, drying oils, e.g. linseed oils, oiticica oil, fish oil, standoil and the like, siccatives, e.g. naphthenoates and the like, stabilization products, e.g. UV absorbers, anti-oxydants and the like, pigments, waxes with high softening points and the like.

EXPERIMENTAL PART

The following examples are intended to illustrate and not to limit the scope of the present invention. Unless otherwise stated all parts therein are by weight.

In the following examples Cemulson NP 8 ® is a Trade Mark of a mixture of addition products of nonylphenols with ethylene oxide, wherein an average of 8 mole of ethylene oxide has been reacted with 1 mole of nonylphenol and Soprophor B ® is a Trade Mark of a mixture of addition products of ricinus oil with ethylene oxide. Octylphenol 8.5 is a mixture of addition products of octylphenols with ethylene oxide, wherein an average of 8.5 moles of ethylene oxide has been reacted with 1 mole of octylphenol.

A. PREPARATION OF ORGANIC CONCENTRATES

Example I formulation 1:
  3.3% w/w of azaconazole
  1.8% w/w of lindane
  50% w/w of 2-butoxyethanol; and
  Cemulsol NP 8 ® ad 100%.
preparation:
  3.3 Parts of azaconazole and 1.8 parts of lindane were added portionwise to 50 parts of 2-butoxyethanol at 50° C. After complete solubilization the mixture was cooled to 25° C. and 44.9 parts of Cemulsol NP 8 ® were added.

Example II

Following the preparation-procedure described in Example I the following formulations were prepared:
formulation 2:
  5% w/w of azaconazole
  50% w/w of 2-butoxyethanol; and
  Cemulsol NP 8 ® ad 100%.
formulation 3:
  1.8% w/w of azaconazole
  3% w/w of lindane
  56% w/w of Soprophor B ®; and
  butyl 2-hydroxyacetic acid ester ad 100 ml.
formulation 4:
  5.0% w/w of azaconazole
  10% w/w of permethrin
  20% of butyl 2-hydroxyacetic acid ester; and
  63.8% w/w of Soprophor B ®;
formulation 5:
  5.0% w/w of azaconazole
  10% w/w of carbosulfan
  20% w/w of butyl 2-hydroxyacetic acid ester and
  63.8% w/w of Cemulsol NP 8 ®.
formulation 6:
  5.0% w/w of azaconazole
  56% w/w Soprophor B ®;
  butyl 2-hydroxyacetic acid ad 100 ml.
formulation 7:
  5.7% w/w of azaconazole
  48.0% w/w of butyl 2-hydroxyacetic acid ester;
  44.3% w/w of Soprophor B ®; and
  2% w/w of colophonium resin.
formulation 8:
  5.7% w/w of azaconazole
  48.0% w/w of butyl 2-hydroxyacetic acid ester;
  44.3% w/w of Soprophor B ®; and
  2% w/w of petroleum resin.
formulation 9:
  5.7% w/w of azaconazole
  48.0% w/w of butyl 2-hydroxyacetic acid ester;
  44.3% w/w of Soprophor B ®; and
  2% w/w of alkyd resin 50 W.
formulation 10:
  5.7% w/w of azaconazole
  45.0% w/w of butyl 2-hydroxyacetic acid ester;
  44.3% w/w of Soprophor B ®; and
  5.0% w/w of alkyd resin 50 W.
formulation 11:
  5.7% w/w of azaconazole
  40.0% w/w of butyl 2-hydroxyacetic acid ester;

44.3% w/w of Soprophor B ®; and
10.0% w/w of alkyd resin 50 W.

formulation 12:
  5.0% w/w of azaconazole
  1.2% w/w of acetic acid;
  40.0% w/w of butyl 2-hydroxyacetic acid ester;
  44.3% w/w of Soprophor B ®; and
  8.8% w/w of alkyd resin 50 W.

formulation 13:
  5% w/w of etaconazole (1-[[2-(2,4-dichlorophenyl)-4-ethyl-1,3-dioxolan-2-yl]methyl]-1H-1,2,4-triazole)
  50% w/w of butoxyethanol; and
  45% w/w of Cemulsol NP 8 ®.

formulation 14:
  10% w/w of etaconazole
  20% w/w of octylphenyl 8.5;
  2% w/w of acetic acid;
  10% w/w of Polysolvan O ®; and
  58% w/w of Cemulsol NP 8 ®.

formulation 15:
  5% w/w of etaconazole
  56% w/w of Soprophor B ®; and
  39% w/w of Polysolvan O ®.

formulation 16:
  5.0% w/w of propiconazole (1-[[2-(2,4-dichlorophenyl)-4-propyl-1,3-dioxolan-2-yl]methyl]-1H-1,2,4-triazole)
  40.7% w/w of butyl 2-hydroxyacetic acid ester;
  44.3% w/w of Soprophor B ®; and
  10% w/w of alkyd resin 50 W.

B. PHYSICAL STABILITY OF THE FORMULATIONS

Example III

100 Parts of formulation 1 was stored during 24 hours at 20° C. and, subsequently, during 24 hours at −7.5° C. The said storage-cycle was repeated during 14 days.

Although some of the formulations crystallized during the storage period at −7.5° C. the mixture always completely homogenized during storage at 20° C. without the precipitation of any crystals.

Example IV

Following the procedure described in Example III the formulations 2–16 were also stored during 14 days at 20° C. and at −7.5° C.

The mixtures completely homogenized during the storage-period at 20° C. without the precipitation of any crystals.

Example V

Aqueous solutions prepared by diluting the formulations 1–16 with distilled water to a final concentration of 100–10.000 ppm of the active ingredient were stored during 24 hours at 20° C. and, subsequently, during 24 hours at −7.5° C. The storage-cycle was repeated during 14 days.

Although most of the aqueous solutions crystallized or became heterogeneous during the storage period at −7.5° C. the solutions homogenized or were easy homogenizable during the storage period at 20° C.

C. UPTAKE BY THE WOOD

Example VI

Wood

Beech wood blocks of 2 cm×2 cm×2 cm were stored until needed in desiccators containing saturated solutions of sodium bichromate, assuring a relative humidity of 52% at room temperature.

Active ingredient formulations

The organic solvent type preservative contained 10 g of azaconazole per liter of a solution consisting of white spirit, plastifying co-solvents and resins. The water-borne type preservatives were prepared as described hereinabove.

Radiolabelled active ingredient

Azaconazole, specifically $^{14}C$-labelled at the 2-ethyl carbon,

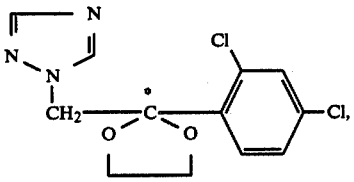

showed a specific activity of 2.22 μCi/mg. Stock solutions containing 2.5 mg $^{14}C$-azaconazole per 25 ml distilled water or 1.25 mg $^{14}C$-azaconazole per 20 ml white spirit were prepared.

Treatment solutions

Since an equal treatment solution strength of 3 g azaconazole per liter was choosen to compare the respective preservative types, the active ingredient formulations were diluted with the appropriate solvents. At the same time radiolabelled active ingredient was spiked in order to facilitate analytical procedures. The composition of the treatment solutions containing azaconazole is given in table 1. Blank treatment solutions were prepared from the blank formulations using identical dilution ratios.

TABLE 1

The composition of the treatment solutions, containing azaconazole as active ingredient, used for dip treatment and impregnation treatment of beech wood blocks. Initial active ingredient concentration of 3000 ppm. Room temperature.

|  | liquid | stock solution A | stock solution B | H₂O ad | White Spirit ad | Xylene ad |
| --- | --- | --- | --- | --- | --- | --- |
| formulation 2 | 15 g | 12.5 ml | — | 250 ml | — | — |
| formulation 6 | 15 g | 12.5 ml | — | 250 ml | — | — |
| Oil based-I | 75 ml | — | 25 ml | — | 250 ml | — |
| Oil based-II | 75 ml | — | 25 ml | — | — | 250 ml |
| Oil based-III | 75 ml | — | 25 ml | — | — | 250 ml |

Stock solution A: 100 μg $^{14}C$—azaconazole/ml distilled water
Stock solution B: 50 μg $^{14}C$—azaconazole/ml white spirit formulation of the oil based—I and oil based—II liquids:
  10 g azaconazole
  50 g colophonium resin
  50 g dibutyl phthalate
  100 ml Polysolvan O ®
  white spirit ad 1000 ml.

formulation of the oil based—III liquid:
- 10 g azaconazole
- 50 g dibutyl phthalate
- 100 ml Polysolvan O ®
- white spirit ad 1000 ml.

METHODS

A. DIP TREATMENT

The humidity conditioned wood blocks were placed individually in pre-weighed and labelled 50-ml glass beakers, and their weight was recorded. Five blocks were dried at 120° C. during 24 hours to assess the 52% relative humidity moisture content. Three cubes were provided for each preservative type-time combination; for each preservative-time combination one cube for blank treatment was included. The blocks were removed from their beakers, while 15-ml portions of the selected treatment solution were added to each beaker. The initial weight of the treatment solution was recorded. The blocks were dipped in the solutions and retained completely immersed by imposing the tip of a Pasteur pipette, fixed into a rack-mounted clamp. Beakers containing organic solvent type preservative were covered with Parafilm to reduce evaporation losses. After the selected contact time intervals, i.e. after 1 hour, 4 hours or 24 hours, the blocks were removed from the solution and fixed in the clamps to leak out. After 15–30 minutes this step was considered to be complete. The final weight of the treatment solution was assessed. After air-drying for 2 hours the treated blocks were placed in pre-weighed and labelled beakers and transferred to the 52% RH desiccator for storage. The desiccator was vented periodically to remove volatilized solvents.

Sample analysis

Treatments solutions

The radioactivity level of the treatment solutions, before and after the dipping treatment, was assayed by liquid scintillation counting (LSC). Solution aliquots of 1 ml were perfectly miscible with 10 ml Insta-Gel II (Packard) scintillator cocktail. A Packard Tri-Carb 4530 microprocessor controlled liquid scintillation spectrometer automatically performing quench and luminescence corrections and converting cpm (counts per minute) into dpm (disintregations per minute) was utilized.

Wood blocks

Five consecutive 2-mm zones were marked on the surface of the blocks in a direction parallel to the wood fibers. The blocks were clamped in a bench-vice and each 2-mm zone was removed by rasping. The shavings were collected on a plastic sheet fixed on the bench-vice.

Quadruplicate 50-mg aliquots per 2-mm section were weighed into combusto-cones (Packard) and combusted in a Packard 306B Sample Oxidizer. The produced $^{14}CO_2$ was trapped in Carbo-Sorb-II (Packard) (7 ml) and radiocounted in Permafluor V (Packard) (12 ml), with the equipment described above.

Calculations

The amount of active ingredient, transferred from the treatment solution to the wood was calculated, starting from the radioactivity mass balance $$W_i \cdot v \cdot dpm_i = W_f \cdot v \cdot dpm_f + dpm_t \quad (1)$$

where $W_i$ equals the initial treatment solution weight (g), $W_f$ the treatment solution weight (g) after dipping, $dpm_i$ and $dpm_f$ the radioactivity levels (dpm/ml) at these procedure steps, $v$ the treatment solution specific volume (ml/g) and $dpm_t$ the total amount of radioactivity transferred from the solution during the dipping. Using the relation between the radioactivity levels of the initial treatment solution, $dpm_i$ (dpm/ml) and its active ingredient concentration, $C_i$ (µg/ml), the total active ingredient transfer was obtained from $$X = dpm_t \cdot C_i \cdot \frac{1}{dpm_i} \quad (2)$$

On, expressing the load of active ingredient per unit weight of dry wood equivalent, $W_b$ (g), and combining equations (1) and (2):

$$X/W_b = (W_i \cdot dpm_i - W_f \cdot dpm_f) \cdot v \cdot C_i \cdot \frac{1}{dpm_i} \cdot \frac{1}{W_b} \text{ (in µg/g)} \quad (3)$$

TABLE 2

Amount of azaconazole (x ± 1 S.D.), expressed in mg per gram oven-dry wood equivalent, transferred to beech blocks during dipping for various time intervals in three different active ingredient formulations. These amounts were calculated from the massa balance of azaconazole in the treating solutions before and after the dipping. Number of replicates = 3. Initial concentration of the treatment solution: 3 g a.i./litre. Room temperature.

|  | t = 1 hour | t = 4 hours | t = 24 hours |
|---|---|---|---|
| Waterborne |  |  |  |
| formulation 2 | 0.608 (±0.008) | 1.019 (±0.039) | 1.858 (±0.297) |
| formulation 6 | 0.924 (±0.162) | 0.952 (±0.119) | 1.810 (±0.376) |
| Organic solvent |  |  |  |
| Oil based I | 0.530 (±0.085) | 0.835 (±0.012) | 1.643 (±0.018) |
| Oil based II | 0.212 (±0.042) | 0.279 (±0.069) | 0.510 (±0.076) |

TABLE 3

Amount of azaconazole a.i. formulation (x ± 1 S.D.), expressed in ml per gram oven-dry wood equivalent, transferred to beech blocks during dipping for various time intervals in three different active ingredient formulations. Number of replicates = 3. Initial concentration of the treatment solution: 3 g a.i./litre. Room temperature.

|  | t = 1 hour | t = 4 hours | t = 24 hours |
|---|---|---|---|
| Waterborne |  |  |  |
| formulation 2 | 0.164 (±0.023) | 0.280 (±0.023) | 0.588 (±0.051) |
| formulation 6 | 0.207 (±0.067) | 0.278 (±0.040) | 0.471 (±0.063) |
| Organic solvent |  |  |  |
| Oil based I | 0.110 (±0.016) | 0.157 (±0.021) | 0.229 (±0.003) |
| Oil based II | 0.102 (±0.021) | 0.130 (±0.024) | 0.232 (±0.027) |

TABLE 4

Estimated concentration of azaconazole (x ± 1 S.D.), expressed in mg per ml impregnated solution, in the solution transferred to beech blocks during dipping for various time intervals in three different active ingredient formulations. Number of replicates = 3. Initial concentration of the treatment solution: 3 g a.i./litre. Room temperature.

|  | t = 1 hour | t = 4 hours | t = 24 hours |
|---|---|---|---|
| Waterborne |  |  |  |
| formulation 2 | 3.737 (±0.468) | 3.755 (±0.223) | 3.145 (±0.236) |
| formulation 6 | 4.654 (±0.710) | 3.463 (±0.077) | 3.944 (±1.061) |
| Organic solvent |  |  |  |

TABLE 4-continued

Estimated concentration of azaconazole (x ± 1 S.D.), expressed in mg per ml impregnated solution, in the solution transferred to beech blocks during dipping for various time intervals in three different active ingredient formulations. Number of replicates = 3. Initial concentration of the treatment solution: 3 g a.i./litre.
Room temperature.

|  | t = 1 hour | t = 4 hours | t = 24 hours |
|---|---|---|---|
| Oil based I | 4.826 (±0.080) | 5.389 (±0.688) | 7.161 (±0.387) |
| Oil based II | 2.089 (±0.254) | 2.118 (±0.171) | 2.189 (±0.079) |

TABLE 5

Amount of azaconazole as a.i., detected at different penetration depths, in beech blocks dipped for 1 hour in three different active ingredient formulations. Cumulative concentration over the whole block. Initial concentration of the treatment solution: 3 g a.i./litre.
Room temperature.

| | penetration depth | | | | |
|---|---|---|---|---|---|
| | 0–2 mm[a] | 2–4 mm[a] | 4–6 mm[a] | 6–8 mm[a] | 8–10 mm[a] | whole block[b] |
| formulation 2 | 1.687 | 0.313 | 0.307 | 0.302 | 0.249 | 0.608 |
| Oil based I | 1.384 | 0.338 | 0.197 | 0.190 | 0.191 | 0.582 |

[a]concentration in mg of azaconazole as a.i. per gram wood at 52% relative humidity
[b]concentration in mg of azaconazole as a.i. per gram oven-dry wood equivalent

B. IMPREGNATION TREATMENT

The dried wood specimens were grouped in 5 sets of 15 pine blocks and 5 sets of 15 beech blocks, one set for each formulation type. A selected group was collected in a beaker, covered with a weight for ballasting, and positioned in a vacuum desiccator. Pressure was reduced to $10^{-3}$ mm Hg by a Leybold-Heraeus S8A vacuum pump. After 15 minutes, 200 ml of the chosen treatment solution was drawn into the desiccator through a tube leading to the beaker. Excessive foaming was avoided. When the blocks were covered, the vacuum was released. The beaker was removed from the desiccator and left for two hours to complete the impregnation. Next, the blocks were lifted from the treatment solution, allowed to drip for 1 minute and weighed (weight after treatment: $W_t$). The blocks were air-dried at room temperature, in a forced ventilation fume-hood for 4 hours. Five blocks were taken at random for analysis, whereas the remaining blocks were stored at 25° C. in the dark for fixation: five blocks were stored for 2 weeks, five blocks for 7 weeks. The outlined procedure was followed for each of the 10 wood-formulation type combinations.

Active ingredient determination

Wood specimen

The concentration of active ingredient in the wood blocks, immediately after treatment was determined by radioassay. The blocks were clamped in a bench-vice and a symmetrical half was removed by rasping. The raspings were collected on a plastic sheet, and homogenized thoroughly. Quadruplicate 50-mg aliquots were weighed into Combusto-Cones (Packard) and combusted in a Packard 306B Sample Oxidiser. The produced $^{14}CO_2$ was trapped in Carbo-Sorb II (Packard) (7 ml) and radiocounted as described hereinbefore in Permafluor V (Packard) (12 ml).

Alternatively, wood raspings were solvent extracted, using dichloromethane for oil based formulations-treated blocks and methanol for water dilutable formulations-treated blocks, in a solvent: solids ratio of 20:1 (v:w). Four consecutive extractions, spread over a 24-h period, were performed. The extracts were combined, adjusted to a known volume and radioassayed as described hereinbefore, using Insta-Gel II (Packard) as scintillation cocktail, added directly to 1-ml aliquots of the methanol extracts or to the solvent evaporation residue of 1 ml-aliquots of the dichloromethane extracts.

The calculated concentration of azaconazole in the wood, $L_w$ (g a.i./kg wood), was obtained as follows:

$$L_w = U \cdot C_o \cdot 1/d_o \cdot 1/W_o \quad (1)$$

where U is the treatment solution uptake (in g per test block), $C_o$ the a.i. concentration in the treatment solution (in g per liter), $d_o$ the density of this solution (in kg per liter) and $W_o$ the weight of the test block (in g). Alternatively, the azaconazole load can be expressed on a volume basis (kg a.i./$m^3$ wood):

$$L_v = U \cdot C_o \cdot 1/d_o \cdot 1/v \quad (2)$$

where V is the volume of the wood blocks (6 $cm^3$).

The determined concentration of azaconazole in the wood, immediately after treatment, was obtained by measuring the radioactivity levels.

TABLE 6

The weight of the test blocks, the uptake of azaconazole formulation during impregnation, and the concentration of active ingredient (a.i.) - expressed in g per kg wood or in kg per $m^3$ wood - calculated from uptake or determined by radioassay (x ± 1 S.D.). Determined azaconazole concentrations are subjected to Duncan's Multiple Range test.

| Wood species | Formulation | Oven-dry weight of blocks $W_o$ (g) | Treatment solution uptake U (g/blocks) | Calculated azaconazole concentration | | Determined azaconazole concentration | |
|---|---|---|---|---|---|---|---|
| | | | | g a.i./kg | kg a.i./$m^3$ | g a.i./kg | kg a.i./$m^3$ |
| PINE | Oil based II | 3.00 (±0.14) | 2.51 (±0.18) | 2.92 (±0.29) | 1.46 (±0.10) | 2.93 (±0.23) | 1.48 (±0.14) |
| | Oil based III | 3.03 (±0.11) | 2.54 (±0.20) | 2.98 (±0.27) | 1.50 (±0.12) | 2.97 (±0.34) | 1.49 (±0.17) |
| | formulation 6 | 3.03 (±0.12) | 4.13 (±0.20) | 4.10 (±0.24) | 2.06 (±0.10) | 4.21 (±0.17) | 2.13 (±0.08) |
| | formulation 9 | 3.04 (±0.14) | 4.13 (±0.25) | 4.09 (±0.37) | 2.06 (±0.12) | 4.23 (±0.53) | 2.19 (±0.21) |
| | formulation 17 | 3.05 (±0.12) | 4.19 (±0.23) | 4.12 (±0.26) | 2.09 (±0.12) | 4.31 (±0.30) | 2.22 (0.13) |
| BEECH | Oil based II | 3.43 (±0.15) | 1.84 (±0.18) | 1.87 (±0.20) | 1.07 (±0.10) | 1.84 (±0.22):B | 1.04 (±0.10) |
| | Oil based III | 3.54 (±0.16) | 2.01 (±0.21) | 2.01 (±0.23) | 1.19 (±0.12) | 1.80 (±0.25):B | 1.04 (±0.12) |
| | formulation 6 | 3.42 (±0.09) | 3.43 (±0.36) | 3.01 (±0.31) | 1.71 (±0.18) | 3.10 (±0.38):A | 1.76 (±0.22) |
| | formulation 9 | 3.49 (±0.10) | 3.45 (±0.56) | 3.01 (±0.52) | 1.72 (±0.28) | 3.05 (±0.62):A | 1.77 (±0.32) |
| | formulation 17 | 3.49 (±0.08) | 3.50 (±0.30) | 3.00 (±0.22) | 1.75 (±0.15) | 3.21 (±0.30):A | 1.85 (±0.20) |

D. EFFICACY

Example VII

I. EXPERIMENTAL PROCEDURE
I.1. Materials
(a) Test fungus:

*Coriolus versicolor* 863 A or *Coniophora puteana* was grown on malt agar at 25° C. in Petri dishes, having a diameter of 120 mm. 20-day-old cultures were used in the test.

(b) Test wood:

Wood blocks (5×2×0.6 cm.) (beech or pine) were used as test material.

(c) Test solutions:

Test solutions were made by dissolving a desired amount of the concerned formulation in distilled water or xylene.

I.2. Methods (a) Treatment of wood blocks with preservatives

Test bocks were oven dried for 18 hours at 100°-110° C., cooled in a desiccator and weighed (i.e. initial dry weight).

Test blocks were weighed down in a Petri dish bottom and placed in a vacuum desiccator. The pressure was reduced to 40 mbar by a water suction pump, the blocks were impregnated with the preservative solution or the blanco solution through a tube leading to the Petri dish.

When the blocks were well covered, vacuum was released, the Petri dish was removed from the desiccator and left for four hours in order to saturate and sterilize the blocks. Control blocks were treated in a similar sterile manner by impregnating the wood blocks with a blanco solution.

Blocks were tamponed with sterile filter paper and weighed under sterile conditions (i.e. weight after treatment).

The amount of preservative taken up by the blocks was calculated (i.e. preservative in wood).

(b) Inoculation of blocks

After drying for six days in a laminar air flow chamber the blocks were transferred to the inoculum Petri dishes and exposed to the attack of *Coriolus versicolor* or *Coniophora puteana* by placing two blocks, one treated with preservative and one control block, on a stainless steel frame in the Petri dish.

Pairs of blocks were chosen in the same weight range.

(c) Duration of test

The test blocks were exposed to fungal attack for 8 weeks at 25° C. Petri dishes were put together in a plastic bag to avoid desiccation.

(d) Examination of test blocks after exposure to fungal attack

The blocks were freed from adhering mycelium, oven dried for 18 hours at 100°-110° C., allowed to cool in a desiccator and weighed (i.e. final dry weight).

II. RESULTS

Table 7 illustrates the toxic thresholds for the aqueous solutions and the oil based mixtures. Toxic threshold as used herein is the amount of azole per m³ of wood preventing the wood from decay in such an amount that 3 percent weight loss is effected.

The percentage of weight loss is found following the formula $$\frac{\text{initial dry weight} - \text{final dry weight}}{\text{initial dry weight}} \cdot 100$$

and the amount of test compound absorbed per m³ of wood is found following the formula $$(\text{weight after treatment} - \text{initial dry weight}) \cdot \frac{C_{sol}}{d_{sol}}.$$

wherein $C_{sol}$ and $d_{sol}$ have the meaning of the concentration of the preservative in the test solution, respectively the density of the test solution.

Since it is irrealistic to define the exact amount of azole/m³ of wood preventing the wood from decay in such an amount that exactly 3 percent weight loss is effected. Table 7 illustrates the range wherein the exact amount is embraced. The said range is limited by a lower amount, i.e. the highest tested amount where more than 3 percent weight loss is effected, and a higher amount, i.e. the lowest tested amount where less than 3 percent weight loss is effected.

TABLE 7

|  |  | Toxic threshold. | |
|---|---|---|---|
|  | diluted with | Coriola versicolor kg azaconazole/m³ | Coniophora puteana kg azaconazole/m³ |
| formulation 2 | water | 0.031–0.057 | 0.537–0.823 |
| formulation 6 | water | 0.033–0.061 | 0.547–0.742 |
| oil-based I | xylene | 0.069–0.143 | 0.940–1.222 |

What we claim is:

1. A water-dilutable wood-preserving liquid containing
   (i) from 10% w/w to 80% w/w of 2-butoxyethanol or butyl 2-hydroxyacetic acid ester;
   (ii) from 20% w/w to 80% w/w of a solubilizer selected from the group consisting of:
      (a) addition products of 1 to 60 moles of ethylene oxide with 1 mole of a phenol which is further substituted with at least one $C_1$–$C_{15}$ alkyl group; and
      (b) addition products of 1 to 60 moles of ethylene oxide with 1 mole of ricinus oil; and
   (ii) from 0.01% w/w to 10% w/w of at least one azole having the formula

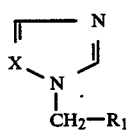

(I)

or an acid addition salt thereof, wherein X is nitrogen or a CH group and $R_1$ is a radical of the formula

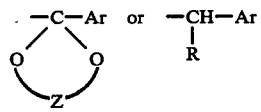

wherein Z is a group —$CH_2$—$CH_2$—, —$CH_2$—$CH_2$—$CH_2$—, —$CH(CH_3)$—$CH(CH_3)$— OR —$CH_2$—$CH(\text{alkyl})$—, wherein said alkyl is a straight or branched $C_1$–$C_{10}$ alkyl radical; said Ar is a phenyl group which is optionally substituted with 1 to 3 halogens, $C_1$–$C_6$ alkyl radicals, $C_1$–$C_6$ alkoxy radicals, cyano-, trifluoromethyl- or nitro groups, a thienyl-, halothienyl-, naphthalenyl- or fluorenyl group; and, said R is $C_1$–$C_{10}$ alkyl, cycloalkyl, cycloalkyllower alkyl, lower alkenyl, aryllower alkyl, aryloxylower alkyl or a radical of the formula —O—R$_o$, wherein said R$_o$ is C$_1$–C$_{10}$ alkyl, lower alkenyl, lower alkynyl or aryllower alkyl, wherein said aryl radical is phenyl, naphthalenyl or substituted phenyl, wherein said substituted phenyl has 1 to 3 substituents selected from the group consisting of halo, cyano, nitro, phenyl, lower alkyl and lower alkoxy, provided that when more than one substituent is present only one thereof may be cyano, nitro or phenyl.

2. A liquid according to claim 1 wherein the azole is selected from the compounds having the formula:

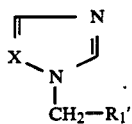  (I-a)

where X is N or CH and R$_1'$ is a radical of the formula

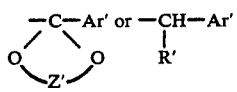

wherein Z' is a group —CH$_2$—CH$_2$—, —CH$_2$—CH$_2$—CH$_2$—, —CH(CH$_3$)—CH$_2$—, —CH(C$_2$H$_5$)—CH$_2$—, —CH(C$_3$H$_7$)—CH$_2$—, —CH(CH$_3$)—CH(CH$_3$)— or —CH(CH$_3$)—CH(C$_2$H$_5$)—; Ar' is unsubstituted phenyl or phenyl substituted with 1 to 3 halogen atoms, preferably chloro atoms, C$_1$–C$_6$ alkyl radicals, C$_1$–C$_6$ alkoxy radicals, cyano or nitro groups; and R' is C$_1$–C$_6$ alkyl or C$_3$–C$_4$ alkenyloxy.

3. A liquid according to claim 1 wherein the azole is selected from the compounds having the formula

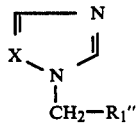  (I-b)

wherein X is N or CH and R$_1''$ is a radical of the formula

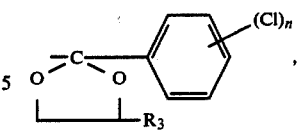

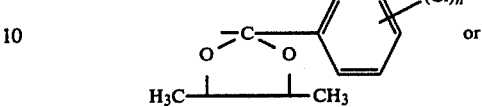 or

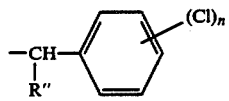

wherein R'' is C$_1$–C$_4$ alkyl, C$_3$–C$_4$ lower alkenyloxy, R$_3$ is hydrogen or C$_1$–C$_3$ alkyl and n is 1 or 2.

4. A liquid according to claim 1 wherein the azole is 1-[2-(2,4-dichlorophenyl)-1,3-dioxolan-2-ylmethyl]-1H-1,2,4-triazole.

5. A liquid according to any one of claims 1 to 4 wherein the solubilizer is selected from the group consisting of:
(i) addition products of 1 to 60 moles of ethylene oxide with 1 mole of nonylphenol or octylphenol; and
(ii) addition products of 1 to 60 moles of ethylene oxide with 1 mole of ricinus oil.

6. An aqueous mixture prepared by diluting a water-dilutable liquid according to any one of claims 1 to 4, for use in the preservation of wood.

7. A water-dilutable wood-preserving liquid containing:
(i) from 10% w/w to 80% w/w of 2-butoxyethanol;
(ii) from 0.01% w/w to 10% w/w of 1-[2-(2,4-dichlorophenyl)-1,3-dioxolan-2-ylmethyl]-1H-1,2,4-triazole or an acid addition salt thereof; and
(iii) a mixture of addition products of nonylphenols with ethylene oxide wherein an average of 8 moles of ethylene oxide has been reacted with 1 mole of nonylphenol, to a total of 100% w/w.

8. A water-dilutable wood-preserving liquid containing:
(i) from 10% w/w to 80% w/w of butyl 2-hydroxyacetic acid ester;
(ii) from 0.01% w/w to 10% w/w of 1-[2-(2,4-dichlorophenyl)-1,3-dioxolan-2-ylmethyl]-1H-1,2,4-triazole or an acid addition salt thereof; and
(iii) a mixture of addition products of ricinus oils with ethylene oxide, to a total of 100% w/w.

* * * * *